US010626376B2

United States Patent
McNally et al.

(10) Patent No.: US 10,626,376 B2
(45) Date of Patent: Apr. 21, 2020

(54) METHOD FOR ISOLATING AND PURIFYING ADENO-ASSOCIATED VIRUS PARTICLES USING SALT

(71) Applicant: St. Jude Children's Research Hospital, Memphis, TN (US)

(72) Inventors: David Joseph McNally, Cordova, TN (US); Bryan Andrew Piras, Memphis, TN (US); Michael Martin Meagher, Cordova, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 114 days.

(21) Appl. No.: 15/350,409

(22) Filed: Nov. 14, 2016

(65) Prior Publication Data
US 2018/0135024 A1  May 17, 2018

(51) Int. Cl.
*C12N 7/02* (2006.01)
*C12N 7/00* (2006.01)

(52) U.S. Cl.
CPC ...... *C12N 7/00* (2013.01); *C12N 2750/14151* (2013.01)

(58) Field of Classification Search
None
See application file for complete search history.

(56) References Cited

U.S. PATENT DOCUMENTS

| | | | |
|---|---|---|---|
| 3,316,153 A | 4/1967 | Van Frank | 167/78 |
| 3,874,999 A | 4/1975 | Zaremba et al. | 435/239 |
| 3,962,421 A | 6/1976 | Neurath | 424/210.1 |
| 4,327,182 A | 4/1982 | Benedictus | 435/239 |
| 4,724,210 A | 2/1988 | Oka et al. | 435/239 |
| 5,506,129 A | 4/1996 | Sangar | 435/239 |
| 6,143,548 A * | 11/2000 | O'Riordan | C12N 7/00 435/235.1 |
| 6,566,118 B1 | 5/2003 | Atkinson et al. | 435/239 |
| 7,419,817 B2 | 9/2008 | Chiorini et al. | 435/239 |
| 7,704,721 B2 | 4/2010 | Wright et al. | 435/239 |
| 7,732,129 B1 * | 6/2010 | Zhang | C07K 14/4746 435/5 |
| 2002/0045250 A1 * | 4/2002 | Wadsworth | C12N 15/86 435/320.1 |
| 2004/0110266 A1 * | 6/2004 | Chiorini | C12N 7/00 435/239 |
| 2005/0186223 A1 | 8/2005 | Williams et al. | 424/209.1 |

(Continued)

FOREIGN PATENT DOCUMENTS

| | | | |
|---|---|---|---|
| WO | 1999/07834 | 2/1999 | |
| WO | WO-0130983 A1 * | 5/2001 | ............... C12N 7/00 |
| WO | 2002/067983 | 9/2002 | |

OTHER PUBLICATIONS

Schagen et al., "Ammonium sulphate precipitation of recombinant adenovirus from culture medium: an easy method to increase the total virus yield," Gene Therapy 7: 1570-1574 (2000).*

(Continued)

*Primary Examiner* — M Franco G Salvoza
(74) *Attorney, Agent, or Firm* — Licata & Tyrrell P.C.

(57) ABSTRACT

Methods for isolating and optionally purifying AAV particles grown in cell cultures using a combination of lyotropic salts, removal of insoluble producer cell debris and DNA, and optional fractionation by hydrophobic interaction chromatography are described.

15 Claims, 1 Drawing Sheet

(56) References Cited

U.S. PATENT DOCUMENTS

| | | | |
|---|---|---|---|
| 2005/0266567 A1 | 12/2005 | Atkinson et al. | 435/456 |
| 2006/0093589 A1* | 5/2006 | Warrington | C12N 15/86 |
| | | | 424/93.21 |
| 2011/0263834 A1* | 10/2011 | Lees | C07K 1/16 |
| | | | 530/399 |
| 2015/0024467 A1 | 1/2015 | Sheldon et al. | 435/239 |
| 2016/0193598 A1* | 7/2016 | Hahn | C07K 1/18 |
| | | | 435/320.1 |

OTHER PUBLICATIONS

Kotin, "Large-scale recombinant adeno-associated virus production," Human Molecular Genetics, vol. 20, Review Issue 1 (Year: 2011).*

Khan et al., "AAV-mediated gene targeting methods for human cells," Nat Protoc 6(4): 482-501 (Year: 2011).*

Fakir, "Construction and optimization of novel recombinant Adeno-Associated Virus rAAV2/5 for targeting microglia to regulate immune responses during neuroinflammation," Submitted Thesis, Victoria University of Wellington (Year: 2014).*

Florencio et al., "Simple downstream process based on detergent treatment improves yield and in vivo transduction efficacy of adeno-associated virus vectors," Molecular Therapy—Methods & Clinical Development 2, 15024 (Year: 2015).*

Breschkin et al. "Hemagglutination variant of measles virus" Virology 1977 80:441-444.

Chahal et al. "Primary recovery and chromatographic purification of adeno-associated virus type 2 produced by baculovirus/insect cell system" J. Virol. Methods 2007 139:61-70.

During et al. "In vivo expression of therapeutic human genes for dopamine production in the caudates of MPTP-treated monkeys using an AAV vector" Gene Therapy 1998 5:820-827.

Lock et al. "Rapid, simple, and versatile manufacturing of recombinant adeno-associated viral vectors at scale" Human Gene Therapy 2010 21(10):1259-1271.

Piras et al. "Systemic Delivery of shRNA by AAV9 Provides Highly Efficient Knockdown of Ubiquitously Expressed GFP in Mouse Heart, but Not Liver" PLoS One 2013 8:1-11.

Piras et al. "Systemic injection of AAV9 carrying a periostin promoter targets gene expression to a myofibroblast-like lineage in mouse hearts after reperfused myocardial infarction" Gene Ther. 2016 23(5):469-78.

Wallis & Melnick "Cationic stabilization—a new property of enteroviruses" Virology 1962 16:504-506.

International Search Report dated Dec. 8, 2017 issued in corresponding PCT application No. PCT/US2017/058210.

International Preliminary Report on Patentability dated May 23, 2019 issued in corresponding PCT application No. PCT/US2017/058210.

* cited by examiner

METHOD FOR ISOLATING AND PURIFYING ADENO-ASSOCIATED VIRUS PARTICLES USING SALT

BACKGROUND

Adeno-Associated Virus (AAV) gene therapy vectors are produced using producer cells grown in culture. Producer cells either release the AAV particles into the cell culture media or they remain associated with the cell, wherein the ratio released to retained AAV particles depends, in part, on the "serotype" of the AAV. Current methods of releasing cell-associated AAV are often time consuming, difficult to scale, or can introduce unwanted and difficult to remove impurities such as detergents.

Various methods have been proposed to improve and/or simplify the recovery of virus or viral products from feedstock. U.S. Pat. No. 3,316,153 describes a multi-step extraction process, aimed at separating virus particles from cellular debris and is assertedly applicable to feedstocks derived from virus-infected chick allantoic fluid or from cell or tissue-culture fluids. In this method, virus adsorbed to precipitated calcium phosphate is dispersed in EDTA at pH 7.8-8.3, causing dissociation and an EDTA-based sequestering of the soluble calcium, thereby releasing the virus for recovery. The resulting virus-containing solution is dialyzed against water or preferably an aqueous glycine-sodium chloride solution to reduce the EDTA and phosphate content.

In U.S. Pat. No. 3,874,999, allantoic fluids containing influenza virus are centrifuged at low speeds to remove gross particles. The virus is then removed from the supernatant by high-speed centrifugation and resuspended in a phosphate buffer. Nonvirus proteins and lipids are removed by treatment of the suspension with 0.1-0.4 M magnesium sulfate at an alkaline pH for 16-18 hours at 4° C. The resultant suspension is clarified by low speed centrifugation and the virus is purified from the resulting supernatant.

U.S. Pat. No. 3,962,421 describes a method for the disruption of influenza viruses. Allantoic fluid is subjected to high-speed centrifugation. The resulting pellet is resuspended in saline and ball-milled for 12-15 hours to create a virus suspension. The virus suspension is then treated with phosphate-ester to disrupt the virus particles into lipid-free particles (subunits) that carry the surface antigens of intact viruses.

In U.S. Pat. No. 4,327,182, allantoic fluid feedstocks from the growth of influenza virus are subjected to a multi-stage extraction process aimed at recovering influenza subunits, haemagglutinin and neuraminidase. The technique relies on a concentration step in which virus feedstock is present with detergent and a saline solution followed by successive filtration to remove non-viral particles.

U.S. Pat. No. 4,724,210 describes methods for purification of influenza using ion exchange chromatography. An influenza-containing solution, e.g., allantoic fluid, is passed through cellulose sulfate column wherein the virus is adhered to the column packing. The column is subsequently washed and virus eluted with a solution containing 1.0 M to 1.5 M sodium chloride. This is followed by a 4.99 M sodium chloride wash.

U.S. Pat. No. 6,566,118 discloses a method of generating a population of recombinant AAV (rAAV) particles by incubating producer cells in a cell culture medium under conditions that promote release of rAAV particles into the medium without lysing the cells. Culture conditions of use in promoting release of rAAV include pH, osmolality (e.g., by using an ionic salt), and temperature.

In WO 1999/07834, herpesvirus infected Vero cell cultures are incubated in a hypertonic aqueous salt solution (0.8 to 0.9 M NaCl) for several hours. The solution is then removed and herpesvirus harvested from the solution. This method is asserted to be superior to methods wherein the cells are subjected to ultrasonic disruption.

US 2005/0186223 discloses a method for dissociating virus from virus-debris complexes by increasing the salt concentration of allantoic fluid. This reference teaches that the salt can be monovalent, divalent or multivalent cation mixtures thereof, e.g., NaCl, KCl, LiCl, $CaCl_2$, MgCl2 and other salts, and can include or exclude ammonium sulfate.

US 2005/0266567 describes methods for generating high titer helper-free preparations of released rAAV vectors using osmolality to release the rAAV from producer cells.

US 2015/0024467 discloses methods of isolating a population of rAAV from in-process impurities by capturing the rAAV particles on an apatite chromatography medium in the presence of polyethylene glycol (PEG). The methods can entail upstream processing such as centrifugation, treatment with BENZONASE®, anion exchange filtration, and/or tangential flow filtration, as well as downstream processing such as heat inactivation, filtration, hydrophobic interaction chromatography, size exclusion chromatography, and/or anion exchange chromatography.

In WO 2002/067983, preparation of a split influenza vaccine is described as involving moderate-speed centrifugation to clarify allantoic fluid, adsorption of the clarified fluid on a $CaHPO_4$ gel, followed by resolublization with an $EDTA-Na_2$ solution. See also WO 02/08749 describing the same process.

During et al. ((1998) *Gene Therapy* 5:820-827) describe the use of a combination of salts (i.e., NaCl, KCl, $CaCl_2$ and $MgCl_2$) to release rAAV from HEK 293 cells.

In Lock, et al. (2010) *Human Gene Therapy* 21(10): 1259-1271), the release of AAV serotypes into culture medium was investigated by the addition of 500 mM NaCl.

Ammonium sulfate has also been suggested for use in concentrating AAV by precipitation (Piras, et al. (2013) *PLoS One* 8:1-11; Piras, et al. (2016) *Gene Ther.* 23(5):469-78). Further, hydrophobic interaction chromatography (HIC) has been suggested for use in the isolation of AAV (Chalal, et al. (2007) *J. Virol. Methods* 139:61-70).

Methods for improving yields by contacting virus-infected cultured cells with elevated salt concentrations have also been described. For example, U.S. Pat. No. 5,506,129 reports increased yields of hepatitis A virus after growing infected BS-C-1 cells in growth medium containing 0.3 M NaCl.

Further, modulation of viral characteristics has been assessed by contacting purified viruses with elevated salt concentrations. In Breschkin et al. ((1977) *Virology* 80:441-444), a particular mutated measles virus lacking hemagglutination activity in isotonic saline exhibited wild-type level hemagglutination activity in 0.8 M $(NH_4)_2SO_4$, whereas the high salt had no effect on the hemagglutination activity of a wild-type virus.

Wallis & Melnick ((1962) *Virology* 16:504-506) reported that, while high salt (1 M $MgCl_2$, 1 M $CaCl_2$, or 2 M NaCl) prevents heat inactivation of polio, coxsackie, and ECHO viruses, 1 M $MgCl_2$ enhances inactivation of adeno-, papova-, herpes-, myxo-, arbor, and poxviruses.

In U.S. Pat. No. 7,704,721, aggregation of purified rAAV virions was prevented by adding at least 200 mM citrate, phosphate, sulfate or magnesium salt to the purified rAAV virions.

SUMMARY OF THE INVENTION

This invention provides a method for isolating AAV particles grown in a cell culture by contacting a suspension of producer cells and AAV particles (e.g., in cell culture medium or buffer) with an effective amount of a lyotropic salt that promotes cell lysis and release of the AAV particles from the producer cells while maintaining producer cell DNA in a substantially intact state; separating insoluble producer cell DNA and cellular debris from the AAV particles; and optionally subjecting the isolated AAV particles to chromatography on a hydrophobic interaction chromatography adsorbent; and optionally recovering an eluate from the hydrophobic interaction chromatography adsorbent that contains substantially purified AAV particles. In some embodiments, the lyotropic salt is at a pH of about 7.0 and includes a cationic component selected from the group of $NH_4^+$, $K^+$, $Na^+$, $Li^+$, $Mg^{2+}$, $Ca^{2+}$ and guanidiunium; and an anionic component selected from the group of $F^-$, $SO_4^{2-}$, $HPO_4^{2-}$, acetate, $Cl^-$, $NO_3^-$, $ClO_3^-$, $I^-$, $ClO_4^-$, and $SCN^-$. In certain embodiments, the lyotropic salt is ammonium sulfate used at concentrations between 250 mM and 2000 mM. In other embodiments, the lyotropic salt is sodium chloride used at a concentration of between 2000 mM and 5000 mM. In further embodiments, the insoluble producer cell DNA and cellular debris are separated from the AAV particles using a physical separation technique such as centrifugation, filtration, skimming, separation funnel separation, mixer-settler separation, and liquid-liquid extraction. In yet other embodiments, the hydrophobic interaction chromatography adsorbent is a membrane or bead matrix with a butyl ligand, octyl ligand, phenyl ligand, bi-phenyl ligand, or combination thereof.

This invention also provides a method for purifying AAV particles grown in a cell culture, which solely includes the steps of contacting a suspension of producer cells and AAV particles with an effective amount of a lyotropic salt that promotes cell lysis and release of the AAV particles from the producer cells while maintaining producer cell DNA in a substantially intact state; separating insoluble producer cell DNA and cellular debris from the AAV particles to obtain isolated AAV particles; subjecting the isolated AAV particles to chromatography on a hydrophobic interaction chromatography adsorbent; and recovering an eluate from the hydrophobic interaction chromatography adsorbent that contains substantially purified AAV particles.

DETAILED DESCRIPTION OF THE INVENTION

Figure 1A:
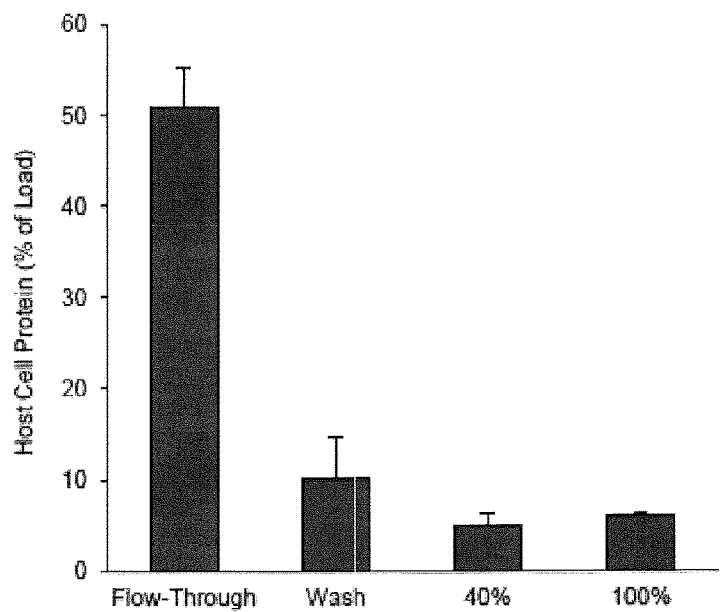
FIG. 1A and FIG. 1B show the host-cell protein, as measured by ELISA (FIG. 1A), and double-stranded DNA, as measured by PICOGREEN (FIG. 1B), in flow-through, wash, 40% elution, and 100% elution fractions as a percentage of material loaded onto a 150 mL phenyl membrane. Lysate was loaded in 1.25 M ammonium sulfate, 20 mM Tris pH 7 and eluted using a step gradient in 40% and 100% 20 mM Tris pH 7. While the 40% elution fraction contained an average of 90% of loaded particles, it contained less than 10% of loaded host-cell protein, and less than 20% of loaded dsDNA (n=2 per fraction).

An integrated method for releasing cell-associated AAV from producer cells and purifying the released AAV has now been developed. It has been found that the addition of ammonium sulfate to producer cell culture medium causes release of cell-associated AAV, likely by inhibiting virus cell-interaction, and physically releasing virus by cell lysis due to osmotic shock. Concurrently, the ammonium sulfate acts to promote hydrophobic interactions with chromatographic ligands for purifying the virus. Accordingly, this invention provides methods for isolating and purifying a population of AAV particles of any AAV capsid serotype from production culture impurities such as damaged AAV particles, helper virus, helper virus proteins, plasmids, cellular proteins and DNA, media components, serum proteins, and the like.

Advantageously, the methods of this invention are cost-effective because the salt used to lyse the cells does not need to be removed or replaced prior to purification via hydrophobic interaction chromatography (HIC) and the method does not require a nuclease or any detergent. Indeed, once the salt is added to culture medium, insoluble host DNA and cellular debris precipitates out and the AAV particles in solution can be isolated from the insoluble material by physical separation techniques such as pipetting or filtration. In addition, the methods of this invention are commercially scalable and provide a population of AAV particles from high titer AAV production culture harvests or feedstreams.

In one aspect, this invention provides a method for isolating AAV particles grown in a cell culture by contacting a suspension of producer cells and AAV particles with an effective amount of a lyotropic salt that promotes cell lysis and release of the AAV particles from the producer cells while maintaining producer cell DNA in a substantially intact state; and separating insoluble producer cell DNA and cellular debris from the AAV particles to obtain isolated AAV particles.

As used herein, "AAV" refers to adeno-associated virus. The term "AAV particles" refers to a complete virus unit. AAV particles include wild-type AAV particles, which include a linear, single-stranded AAV nucleic acid genome associated with at least one AAV capsid protein coat, as well as recombinant AAV (rAAV) particles, which are infectious viral particles containing a heterologous DNA molecule of interest flanked on both sides by AAV inverted terminal repeats (ITRs). In some embodiments of this invention, rAAV particles are produced in a suitable producer cell, which contains an AAV vector, AAV helper functions and accessory functions. In this manner, the producer cell is rendered capable of encoding AAV polypeptides that are required for packaging the recombinant AAV vector into recombinant virion particles for subsequent gene therapy applications.

The present invention is not limited to an AAV particle of any specific serotype. Thus, an AAV particle of this invention includes any serotype, which has been isolated from human (AAV of serotypes 2, 3, 5, 6, and 9) and non-human primate samples (AAV of serotypes 1, 4, 7, 8, 10), as well as AAV of serotypes 11, 12, 13, 14, 15, or 16 and hybrid serotypes such as LK03, S3 and the like. However, in certain embodiments, this invention is particularly useful in the preparation of AAV particles of the human serotypes, more preferably for AAV of human serotypes 3, 5 and 8, most preferably for AAV of human serotype 3.

A "producer cell" or "host cell" is a cell or cell line used for AAV particle replication and packaging. Such a producer cell (usually a mammalian or insect host cell) generally includes, or is modified to include, several different types of components for AAV production. The first component is an adeno-associated viral vector genome (or AAV pro-vector) that can be replicated and packaged into particles by the host packaging cell. The AAV pro-vector will normally include a heterologous polynucleotide (or "transgene"), with which it is desired to genetically alter another cell in the context of gene therapy (since the packaging of such a transgene into AAV particles can be effectively used to deliver the transgene to a variety of mammalian cells). The transgene is generally flanked by two AAV ITRs, which include sequences that are recognized during replication and packaging of the AAV vector, as well as during integration of the vector into a host cell genome. A second component is a helper virus that can provide helper functions for AAV replication. Although adenovirus has been employed, other helper viruses can also be used as is known in the art. Alternatively, the requisite helper virus functions can be isolated genetically from a helper virus and the encoding genes can be used to provide helper virus functions in trans. The AAV vector elements and the helper virus (or helper virus functions) can be introduced into the producer cell either simultaneously or sequentially in any order. The final components for AAV production to be provided in the producer cell are "AAV packaging genes" such as AAV rep and cap genes that provide replication and encapsidation proteins, respectively. Several different versions of AAV packaging genes can be provided (including wild-type rep-cap cassettes as well as modified rep and/or cap cassettes in which the rep and/or cap genes can be left under the control of the native promoters or operably linked to heterologous promoters). Such AAV packaging genes can be introduced either transiently or stably into the host cell, as is known in the art. Examples of suitable producer cells include, for example, human-derived cell lines such as HeLa, A549, or 293 cells, or insect-derived cell lines such as SF-9, in the case of baculovirus production systems.

Any suitable cell culture media known in the art may be used for the production of AAV particles by producer cells. These media include, without limitation, media produced by Hyclone Laboratories and JRH including Modified Eagle Medium (MEM), Dulbecco's Modified Eagle Medium (DMEM), custom formulations such as those described in U.S. Pat. No. 6,566,118, and Sf-900 II SFM media as described in U.S. Pat. No. 6,723,551, each of which is incorporated herein by reference in its entirety, particularly with respect to custom media formulations for use in production of recombinant AAV particles.

AAV production culture media may be supplemented with serum or serum-derived recombinant proteins at a level of 0.5%-20% (v/v or w/w). Alternatively, as is known in the art, AAV particles may be produced in serum-free conditions which may also be referred to as media with no animal-derived products. One of ordinary skill in the art will appreciate that commercial or custom media designed to support production of AAV particles may also be supplemented with one or more cell culture components known in the art, including without limitation glucose, vitamins, amino acids, and or growth factors, in order to increase the titer of AAV particles in production cultures.

AAV production cultures can be grown under a variety of conditions (over a wide temperature range, for varying lengths of time, and the like) suitable to the particular producer cell being utilized. As is known in the art, AAV production cultures include attachment-dependent cultures, which can be cultured in suitable attachment-dependent vessels such as, for example, roller bottles, hollow fiber filters, microcarriers, and packed-bed or fluidized-bed bioreactors. AAV vector production cultures may also include suspension-adapted producer cells such as HeLa, 293, and SF-9 cells, which can be cultured in a variety of ways including, for example, spinner flasks, stirred tank bioreactors, and disposable systems such as the WAVE bag system.

In accordance with the present method, AAV particles are isolated from production cultures by contacting a suspension of producer cells and AAV particles with an effective amount of a lyotropic salt. The term "isolated," as used herein, refers to a preparation of AAV particles, which is substantially devoid of insoluble producer cell DNA and cellular debris. Thus, for example, isolated AAV particles may be prepared to enrich for AAV particles from a source mixture, such as a culture lysate or production culture supernatant. Enrichment can be measured in a variety of ways, such as, for example, by infectivity, or by assaying for potentially interfering substances present in the source mixture, such as impurities, including production culture impurities or in-process impurities, including producer cell DNA or protein. Cellular protein impurities can generally be observed as the presence of COOMASSIE staining bands on SDS gels.

In some embodiments, the suspension of producer cells and AAV particles includes the spent cell culture medium. In other embodiments, the cell culture medium has been separated from the cells and the cells and cell culture medium are processed separately to isolate AAV particles. In accordance with this embodiment, the suspension of producer cells and AAV particles may be suspended in a buffer, e.g., phosphate-buffered saline or Tris.

Of significance, the present method does not use freeze/thaw cycles, sonication, microfluidization, detergents, nucleases, proteases or organic solvents in the lysis of the producer cells. Rather, the lyotropic salt promotes cell lysis and release of the AAV particles from the producer cells while maintaining producer cell DNA in a substantially intact state. Producer cell DNA is in a substantially intact state when it is not degraded into fragments and can be readily separated from the AAV particles.

As used herein, the term "lyotropic" refers to the influence of different salts on hydrophobic interactions, more specifically the degree to which an anion increases the salting out effect on proteins, or for cations, increases the salting-in effect on proteins according to the Hofmeister series of salt effects (Queiroz, et al. (2001) *J. Biotechnology* 87:143-159; Palman, et al. (1977) *J. Chromatography* 131:99-108; Roe, et al. (1989) Protein Purification Methods: A Practical Approach. IRL Press Oxford, pp. 221-232). The series for anions in order of decreasing salting-out effect is: $PO_4^{3-}$>$SO_4^{2-}$>$CH_3COO^-$>$Cl^-$>$Br^-$>$NO_3^-$>$ClO_4^-$>$I^-$>$SCN^-$, while the series for cations in order of increasing salting-in effect: $NH_4^+$>$Rb^+$>$K^+$>$Na^+$>$Cs^+$>$Li^+$>$Mg^{2+}$>$Ca^{2+}$>$Ba^{2+}$. According to the present invention, a "lyotropic salt" is a salt that has the property of promoting the precipitation or salting-out of certain types of high molecular weight species, in particular proteins, from aqueous solution. In certain embodiments, the lyotropic salt has a cationic component selected from the group of ammonium, potassium, sodium, lithium, magnesium, calcium and guanidiunium. In other embodiments, the lyotropic salt has an anionic component selected from the group of fluoride, sulfate, phosphate, acetate, chloride, nitrate, chlorate, iodide, perchlorate, and thiocyanate. In some embodiments, the lyotropic salt is an ammonium, potassium or sodium salt. In other embodiments, the lyotropic salt is a sulfate, phosphate or chloride salt. Lyotropic salts of particular use in the method of this invention include ammonium sulfate, ammonium citrate, sodium sulfate, sodium citrate, potassium sulfate, potassium citrate, potassium phosphate, potassium chloride, sodium chloride, and combinations thereof. In particular embodiments, the lyotropic salt is ammonium sulfate.

An effective amount of a lyotropic salt is an amount that promotes cell lysis of producer cells and release of the AAV particles from the producer cells while maintaining producer cell DNA in a substantially intact state. The effective amount can be determined by titrating the lyotropic salt and measuring membrane integrity (e.g., by trypan blue dye exclusion) as an indicator of cell lysis; intact viral capsids (e.g., by ELISA) or viral DNA (e.g., by slot blot) as an indicator of the release of AAV particles; and producer cell DNA integrity (e.g., by gel electrophoresis). Using such analysis, the minimum amount of ammonium sulfate needed for AAV release was determined. Samples were harvested, lysed using varying amounts of ammonium sulfate (1250 mM, 750 mM, 500 mM, 250 mM, 100 mM, 50 mM and 0 mM), and analyzed by ELISA for total capsids. The results indicated that samples treated with 500 mM to 1250 mM ammonium sulfate released between about $65 \times 10^{11}$ to about $75 \times 10^{11}$ total capsids whereas samples treated with 50 to 250 mM ammonium sulfate released between about $45 \times 10^{11}$ to about $50 \times 10^{11}$ total capsids. By comparison, samples treated with 0 mM ammonium sulfate released about $12 \times 10^{11}$ total capsids. This analysis demonstrated that the amount of ammonium sulfate needed to effectively release AAV was at least about 250 mM.

Accordingly, an effective amount of a lyotropic salt is in the range of between 250 mM to 5000 mM, 500 mM to 4000 mM, 1000 mM to 4000 mM, 1000 mM to 3000 mM, or 1000 mM to 2000 mM. By way of illustration, when the lyotropic salt is ammonium sulfate, an effective amount can be in the range of 250 mM to 2000 mM. Further, when the lyotropic salt is sodium chloride, an effective amount can be in the range of 3000 mM to 5000 mM. More preferably, when the lyotropic salt is ammonium sulfate, an effective amount can be in the range of 1000 mM to 2000 mM. The pH of the lyotropic salt is preferably in the range of about 5 to 9 (±0.1, 0.2, 0.3, 0.4 or 0.5). More preferably, the pH of the lytropic salt is in the range of about 6 to 8 (±0.1, 0.2, 0.3, 0.4 or 0.5). Most preferably, the pH of the lytropic salt is about 7 (±0.1, 0.2, 0.3, 0.4 or 0.5).

After addition and thorough mixing of the lyotropic salt with the suspension of producer cells and AAV particles, the mixture is incubated for a sufficient of amount of time to lyse the cells and obtain at least two phases, one containing insoluble producer cell DNA and cellular debris (i.e., a white non-aqueous layer that rises to the top of the mixture) and the other containing the majority of AAV particles. A "sufficient amount of time" can be determined empirically by monitoring cell lysis and phase separation. Alternatively, a "sufficient amount of time" can be between about 8 to 24 hours, or more preferably between 15 and 19 hours. To facilitate separation, the mixture is incubated without agitation. Moreover, in certain embodiments, incubation is carried out at or below room temperature, preferably at 15° C., 10° C., or 4° C.

Once phase separation occurs insoluble producer cell DNA and cellular debris is separated from the AAV particles using, e.g., a physical separation technique. Examples of such techniques include, but are not limited centrifugation, filtration, pipetting, skimming, separation funnel separation, mixer-settler separation, and liquid-liquid extraction. By way of illustration, filtration can be carried out through a cellulose acetate filter of 0.2 µm or greater pore size known in the art. Using such separation techniques the AAV particles in solution (e.g., in buffer or cell culture medium) are isolated from the producer cells and can be used as is or further purified to remove impurities or contaminants such as medium components, salts, low molecular weight proteins, and the like.

To further purify the AAV particles, the present method provides the additional steps of subjecting the isolated AAV particles to chromatography on a hydrophobic interaction chromatography adsorbent; and recovering an eluate from the hydrophobic interaction chromatography adsorbent that contains substantially purified AAV particles. For the purposes of this invention, the term "purified," "purifying" or "substantially purified" refers to AAV particles that may be substantially or essentially free of soluble components (i.e., components remaining after salting-out insoluble components) that are normally present in a producer cell culture, i.e., producer cell molecules such as proteins, carbohydrates, lipids, plasmid DNA, and/or carrier virus DNA; medium components such as vitamins, salts, peptides, serum proteins and/or sugars; and/or helper virus molecules such as helper virus proteins and/or helper virus DNA. AAV particle preparations that may be substantially free of components of a producer cell culture include preparations of AAV particles having less than about 30%, less than about 25%, less than about 20%, less than about 15%, less than about 10%, less than about 5%, less than about 4%, less than about 3%, less than about 2%, or less than about 1% (by dry weight) of impurities.

Hydrophobic interaction chromatography (HIC) is a technique for separating biomolecules based on differences in their surface hydrophobicity. HIC adsorbents contain hydrophobic ligands such as linear chain hydrocarbons (e.g., propyl (C3), butyl (C4), hexyl (C6), or octyl (C8)), aromatics (e.g., phenyl or bi-phenyl) or a combination thereof. In certain embodiments of the instant method, the HIC adsorbent has an aromatic ligand. In particular embodiments, the ligand of the HIC adsorbent is a phenyl group. In pure water, the hydrophobic effect is too weak for functional interaction between the ligand and proteins, or between the proteins themselves. However, lyotropic salts enhance hydrophobic interactions, and the addition of salt drives the capture of proteins to HIC adsorbents. For this reason, HIC resins are usually loaded under high salt concentrations and eluted at lower salt concentrations. In this respect, subsequent to removing the insoluble material cellular debris and DNA, the isolated AAV particles, in a high concentration of lyotropic salt, can be directly applied to the HIC adsorbent.

Ligands of the HIC adsorbents can be attached to any suitable support or matrix known in the art. In some embodiments, a bead-based matrix is used. Examples of suitable HIC resins include, without limitation, GE Healthcare HIC Resins such as Butyl SEPHAROSE 4 Fast Flow (FF), Butyl-S SEPHAROSE FF, Octyl SEPHAROSE 4 FF, Phenyl SEPHAROSE BB, Phenyl SEPHAROSE HP, Phenyl SEPHAROSE 6 FF High Sub, Phenyl SEPHAROSE 6 FF Low Sub, Source 15 ISO (isopropyl), Source 15 PHE (phenyl), CAPTO Phenyl, CAPTO Butyl, and SREAMLINE Phenyl; Tosoh HIC Resins such as TSKgel Ether-5PW, TSKgel Phenyl-5PW, TOYOPEARL Phenyl-650, TOYOPEARL Butyl-650, TOYOPEARL, Butyl-600 and TOYOPEARL Phenyl-600; Waters HIC Resins such as YMC-PACK Octyl Columns, YMC-PACK Phenyl Columns, and YMC-PACK Butyl Columns; JNC Corporation HIC Resins such as CELLUFINE Butyl, CELLUFINE Octyl, and CELLUFINE Phenyl; JT Baker HIC Resin such as BAKERBOND Poly HI-PROPYL media; Biorad HIC Resins such as MACRO-PREP t-Butyl and MACRO-PREP methyl resins; and Applied Biosystems HIC Resin such as the POROS® HP2 resin.

In other embodiments, membrane chromatography is used. Membrane-based chromatography sorbents are of particular interest in the purification of viral gene therapy vectors due to their large pores, dependence on convective mass transfer, and high flow rates (Kutner, et al. (2009) *BMC Biotechnol.* 9:10; McNally, et al. (2014) *J. Chromatogr. A* 1340:24-32). Examples of suitable HIC membranes include, without limitation, GE Healthcare HIC membranes such as READYTOPROCESS ADSORBER Phen and PREDICTOR ADSORBER Phen membranes and Satorius membranes such as SARTOBIND Phenyl.

Recovery of AAV particles from the HIC adsorbent is achieved by adding a low salt buffer to the HIC adsorbent to elute the AAV particles. A low salt buffer is generally provided at a concentration less than the lyotropic salt concentration used to bind the AAV particle to the HIC adsorbent. In some embodiments, the elution salt buffer contains less than 1000 mM, less than 900 mM, less than 800 mM, less than 700 mM, less than 600 mM, less than 500 mM, less than 100 mM, or less than 50 mM lyotropic salt. In other embodiments, the low salt buffer contains 0 mM lyotropic salt. In certain embodiments, the low salt buffer is phosphate-buffered saline (PBS) or Tris-HCl at a pH in the range of, but not limited to, 6 to 8, preferably about 7. Other buffers are known to those skilled in the art, such as, but not limited to, TES (N-tris(hydroxymethyl)methyl-2-aminoethane-sulfonic acid), Tricine (N-tris(hydroxymethyl) methyl-glycine), PIPES (Piperazine-N,N-bis(2-ethane sulfonic acid), MOPS (3-(N-morpholino)-propanesulfonic acid), MES (2-(N-morpholino)-ethanesulfonic acid), HEPES N-(2-hydroxyethyl)piperazine-N'-(2-ethanesulfonic acid), and Bicine (N,N-bis(2-hyroxyethyl) glycine) may be used. The low salt buffer can be applied to the HIC adsorbent as a step or linear gradient, as is conventional in the chromatographic arts. In some embodiments, it is preferred that the low salt buffer elutes the AAV particles without eluting AAV particles with empty capsids, partially denatured capsids, less infectious capsids, and/or partially full capsids. Fractions eluted from the HIC adsorbent can be tested for the presence and purity of AAV particles as described herein.

As described herein, the method of this invention can be used for the isolation of AAV particles from insoluble producer cell debris and DNA. However, in other embodiments of this invention, the AAV particles are both isolated and purified. Accordingly, this invention also provides a method for purifying AAV particles grown in a cell culture, wherein the method consists of or consists essentially of the steps of contacting a suspension of producer cells and AAV particles with an effective amount of a lyotropic salt that promotes cell lysis and release of the AAV particles from the producer cells while maintaining producer cell DNA in a substantially intact state; separating insoluble producer cell DNA and cellular debris from the AAV particles to obtain isolated AAV particles; subjecting the isolated AAV particles to chromatography on a hydrophobic interaction chromatography adsorbent; and recovering an eluate from the hydrophobic interaction chromatography adsorbent that contains substantially purified AAV particles. Advantageously, this method of the invention is carried out in the absence of freeze/thaw cycles, sonication, microfluidization, detergents, nucleases, proteases or organic solvents and can be readily used to purify any serotype of AAV or rAAV.

Using the method of this invention, at least about 70%, 75%, 80%, 85%, 90%, 910, 92%, 93%, 94%, 95%, 96%, 97%, 98%, 99% or 100% of AAV or rAAV can be recovered from cell lysate and/or medium loaded on a hydrophobic interaction chromatography adsorbent. Therefore, the method described herein provides for highly efficient, direct capture and elution of AAV particles from both cell culture media and cell lysates. Furthermore, using a hydrophobic interaction chromatography adsorbent, it is possible to effectively capture and elute multiple serotypes of AAV with high recoveries, thereby providing a serotype-independent method of AAV harvest and purification.

The following non-limiting examples are provided to further illustrate the present invention.

Example 1: Materials and Methods

Chemicals and Reagents.

All chemicals were purchased from Sigma Aldrich and were of molecular biology grade or higher.

Cell Culture and Transfection.

Adherent HEK 293T/17 cells were cultured in 10 cm plates or 10-layer cell stack (Corning Inc., Corning, N.Y.) and transfected using serum-free Dulbecco's Modified Eagle's Medium (DMEM) or DMEM supplemented with 1-5% fetal bovine serum (FBS) and 2 mM GLUTAMAX (L-alanyl-L-glutamine dipeptide; Life Technologies Inc., Grand Island, N.Y.). AAV was produced by two-plasmid transfection using PEIPRO (polyethylenimine-based transfection reagent; Polyplus-transfection SA, Illkirch, France) one day after seeding cells at a density of $7.26 \times 10^4$ cells/$cm^2$. Viral genomes flanked by AAV2 ITRs were packaged into AAV1, AAV3-like, AAV5, or AAV8 capsids. Cell cultures were maintained from between 3 and 6 days post-transfection.

AAV Harvest.

At the time of harvest, culture media were pipetted off plates or decanted from individual cell factories, after which cells were detached using PBS with 5 mM EDTA (PBS-EDTA). Cells were lysed via freeze/thaw or chemical means. For freeze/thaw, the cells were pelleted, resuspended in TD buffer (phosphate buffer with $MgCl_2$ and KCl), and subjected to 5 freeze/thaw cycles. For chemical lysis the cells were incubated with high concentrations of salt. This was either performed directly on a 10 cm plate by adding 1.25 M ammonium sulfate or 5 M NaCl to the cell culture plate or via the addition of a concentrated 3.5 M ammonium sulfate solution to cells harvested in PBS-EDTA to a final concentration of 1.25 M ammonium sulfate. Following harvest, media or cell lysate were filtered with a minimum pore size of 0.22 μm. If a non-aqueous phase developed it was removed via physical separation, e.g., pipetting.

AAV Capsid ELISA.

Assembled AAV particles were detected using the AAV1, AAV5, or AAV8 Titration ELISA Kit (PRAAV1, PRAAV5, and PRAAV8; Progen Biotechnik GmbH, Heidelberg, Germany). Briefly, samples were diluted in kit-provided sample buffer and incubated on the provided ELISA plate for one hour. Plates were then incubated with biotin-conjugated anti-AAV1, anti-AAV5, or anti-AAV8, followed by a streptavidin peroxidase conjugate, and a substrate containing tetramethylbenzidine. Absorbance was measured on a SPECTRAMAX M2 spectrophotometer (Molecular Devices, LLC, Sunnyvale, Calif.) at 450 nm.

Double-Stranded Deoxyribonucleic Acid and Host Cell Protein Analysis.

Double-stranded DNA concentration was measured with the QUANT-IT PICOGREEN® double-stranded DNA (ds-DNA) Assay Kit (Thermo Fisher Scientific, Waltham, Mass.). HEK293T/17 host cell protein was determined using a HEK 293 Host Cell Protein ELISA kit (Cygnus Technologies, Southport, N.C.) per manufacturer's instruction.

Chromatography.

Filtered cell culture medium or lysate was applied to the following membrane adsorbers: SARTOBIND STIC-PA, a primary amine ligand; SARTOBIND Q, a quaternary amine ligand; SARTOBIND S, a methyl sulfonate ligand; or SARTOBIND Phenyl, a phenyl ligand (Sartorius Stedim North America Inc., Bohemia, N.Y.); using an ÄKTAexplorer 100 or ÄKTA Avant chromatography systems (GE Healthcare Life Sciences, Little Chalfont, United Kingdom).

Ion-Exchange Membranes.

AAV8-containing cell culture medium was treated with 10 U/mL BENZONASE nuclease for 1 hour at 37° C. and filtered using 0.22 μm STERICUPS (EMD Millipore, Darmstadt, Germany). This was either titrated to pH 6.0 in the case of the SARTOBIND S membrane or directly applied to the membrane. SARTOBIND STIC-PA and SARTOBIND Q membranes were run at a flow rate of 30 MV/minute. SARTOBIND S membranes were run at a flow rate of at 5 MV/minute. The buffers used for SARTOBIND STIC-PA and SARTOBIND Q membranes runs were Buffer A: 10 mM BTP, 10 mM Tris, pH 9.0 or pH 7.0; and Buffer B: 2 or 3 M NaCl, 10 mM BTP, 10 mM Tris, pH 9.0 or pH 7.0. The buffers used for SARTOBIND S membranes were 20 mM BTP, pH 6.0, and 1 M NaCl+20 mM BTP, pH 6.0. Following loading of material, the membranes were washed and eluted using a gradient of Buffers A and B. Fractions were taken during load, wash and elution steps.

Hydrophobic Interaction Membrane.

AAV-containing samples titrated to 1, 1.25, or 1.5 M ammonium sulfate and 20 mM Tris pH 6.5, 7.0 or 7.5 were applied to the phenyl membranes and were run at a flow rate of between 1.7 and 5 MV/minute. Buffers used included Buffer A: 1, 1.25, or 1.5 M ammonium sulfate and 20 mM Tris, pH 6.5, 7.0 or 7.5; and Buffer B: 20 mM Tris, pH 6.5, 7.0 or 7.5. Following loading of material, the membranes were washed and eluted using a gradient of Buffers A and B. The design of experiments (DoE) was generated and analyzed using MODDE 10 (Umetrics AB, Umea, Sweden).

Statistics.

Data are expressed as the average plus or minus the standard deviation, where appropriate. Analysis was performed in EXCEL (Microsoft Corp., Redmond, Wash.) with one-way ANOVA with a Tukey comparison where appropriate. $P<0.05$ was considered significant in all comparisons.

Example 2: Screening Ion-Exchange Membrane Adsorbers for AAV8 Binding and Elution AAV8 was harvested from cell culture media, clarified, and applied to quaternary amine (Q), methyl sulfonate (S) and primary amine (PA) ion-exchange membranes to assess their ability to bind and elute AAV8. In order to minimize pre-processing, adjustment of pH and conductivity of the AAV8-containing cell culture media was not performed, except in the case of the S membrane in which the medium was adjusted to pH 6.0. Bound species were eluted from the Q and PA membranes using 2 M NaCl, 10 mM BTP, 10 mM Tris pH 9.0, or for the S membrane using 1 M NaCl, 20 mM BTP pH 6.0, and AAV8 capsid ELISA was used to assess recovery. The amount of AAV8 detected in the flow-through and elution fractions differed depending on the ligand chemistry of the membrane. 78% of AAV8 particles loaded onto the Q membrane and 73% of particles loaded onto the S membrane were found in the flow-through, with 9% and 15% in the elution fractions, respectively. However, the PA membrane performed significantly better at capturing AAV8 particles, with only 0.01% of loaded AAV8 found in the flow-through and 67% of particles in the elution fraction.

Example 3: Efficient Recovery of AAV8 from a Primary Amine Membrane Adsorber

AAV8 was harvested from cell culture medium, clarified, and directly applied to a PA membrane. The membrane was then eluted with 2 M or 3 M NaCl, 10 mM BTP, 10 mM Tris at either pH 9 or pH 7, and AAV8 capsid ELISA was used to assess recovery. Increasing the eluent NaCl concentration from 2 M to 3 M led to an increased recovery of 83%. Furthermore, reducing the pH from 9 to 7 led to an increased recovery of 94%. To assess the practicality of using a PA membrane in large-scale processing, the binding capacity for AAV8 was determined. This was performed by overloading the membrane and collecting the flow-through to determine the break-through point of AAV8. It was found that the dynamic binding capacity per mL of membrane was approximately $1\times10^{14}$ AAV8 particles.

Example 4: Screening a Hydrophobic Interaction Membrane Adsorber for AAV8 Binding and Elution AAV8 was harvested from cell culture medium, clarified, and adjusted to 1.5 M ammonium sulfate, 20 mM Tris-HCl pH 7.5. The adjusted cell culture medium was then applied to a phenyl membrane and eluted using 10 mM BTP, 10 mM Tris, pH 7.5, and AAV8 capsid ELISA was used to assess recovery. Over two runs, an average of 3% of loaded AAV8 capsids were detected in the flow-through while an average of 101% of loaded capsids were found in the eluate.

Example 5: Efficient AAV8 Recovery from a Hydrophobic Interaction Membrane Adsorber Via Design of Experiment Methodology A two-factor, two-level full factorial design was generated using MODDE to examine the pH, from 6.5-7.5, and ammonium sulfate concentration, from 1.0-1.5 M, for efficiently recovering AAV from a phenyl membrane. Specifically, media was adjusted to either 1, 1.25, or 1.5 M ammonium sulfate at either pH 6.5, 7.0, or 7.5 and eluted with 20 mM Tris pH 6.5, 7.0, or 7.5, respectively. Recovery was assessed by AAV8 capsid ELISA.

This analysis indicated that at 1.5 M ammonium sulfate, pH 7.5, 110% (n=1) of loaded capsids were recovered in the elution fraction. This fell to 89% (n=1) for 1.5 M, pH 6.5. By contrast, 1 M ammonium sulfate at pH 6.5 and 7.5 led to recoveries of only 38% (n=1) in the elution fraction, with 41-57% of capsids in the flow-through. However, a midpoint of 1.25 M ammonium sulfate at pH 7 led to a recovery of 104±4.4% (n=3) of loaded AAV8 capsids in the elution fraction.

Example 6: Effective Release of Cell-Associated AAV Particles

Four duplicate sets of 10 cm tissue culture plates of HEK293T/17 cells were cultured to produce AAV3-like particles, which, in contrast to AAV, associate more closely with cells than with culture media. Cells were harvested three days post-transfection and lysed via (1) repeated cycles of freeze/thaw; (2) addition of 5 M NaCl; (3) addition of 1.25 M Ammonium Sulfate; or (4) addition of 10 mM BTP, 10 mM Tris, pH 9. The total quantity of released capsids was assessed by AAV8 capsid ELISA, to which the AAV3-like hybrid particles were able to bind.

This analysis indicated that $8.6\pm0.68\times10^{12}$ particles, $8.4\pm0.48\times10^{12}$ particles, $7.0\pm0.0.02\times10^{12}$ particles, and $3.8\pm0.76\times10^{11}$* particles were recovered, respectively, by freeze/thaw, 5 M NaCl, 1.25 M ammonium sulfate, and 10 mM BTP, showing that salt could be used to effect AAV particle release from cells (n=2 per group, * denotes statistically significant difference as measured by one-way ANOVA with Tukey post-hoc analysis).

Example 7: Direct Application of AAV Containing Lysate to a Hydrophobic Interaction Membrane The lysate obtained in Example 6 was filtered and directly loaded onto a phenyl membrane or, in the case of the 5 M NaCl lysate, directly loaded or diluted to 3 M NaCl and then loaded. The recovered AAV was assessed through AAV8 capsid ELISA. This analysis indicated the material lysed in 1.25 M ammonium sulfate and loaded directly onto the membrane had an average recovery of 97%, while the 5 M NaCl lysate yielded only 28% and the sample diluted to 3 M NaCl yielded only 13% of loaded particles. Therefore, 1.25 M ammonium sulfate was used for all subsequent experiments with the phenyl membrane.

Example 8: Determination of the Dynamic Binding Capacity of a Hydrophobic Interaction Membrane for AAV Particles AAV8 or AAV3-like particle-containing cell culture medium with or without serum, cell lysate, or a combination of lysate and culture media was generated through culture and transient transfection of HEK293T/17 cells. These fractions were then applied to a phenyl membrane and the concentration of AAV capsids in the flow-through was measured using AAV8 capsid ELISA, which allowed the dynamic capacity of the membrane for AAV capsids to be assessed. The breakthrough curve for AAV8 in cell culture media with 1% serum demonstrated a dynamic capacity at 10% breakthrough of approximately $2\times10^{13}$ capsids/mL of membrane. Similarly, the breakthrough curve of lysate containing AAV3-like particles demonstrated a dynamic capacity of $1\times10^{13}$ capsids/mL of membrane.

Example 9: Phase Separation of Nucleic Acids from AAV Capsids During Lysis

A 10-layer cell stack containing HEK293T/17 cells was cultured and transfected with plasmids required for AAV3-like particle production. Three days post-transfection, the cell culture medium was removed and the cells were harvested using a PBS-EDTA solution. A 3.5 M ammonium sulfate solution was added to the PBS-EDTA/cell mixture to a final concentration of 1.25 M ammonium sulfate and was mixed thoroughly. This mixture was then incubated at 4° C. for between 15 and 19 hours without agitation. During incubation a phase separation occurred and a white non-aqueous layer formed at the top of the lysate/ammonium sulfate mixture. This non-aqueous material can be removed via physical separation, e.g., pipetting. Notably, dispersion of this non-aqueous material occurs when treated with BENZONASE nuclease for 1 hour at 37° C. compared to a nuclease-free control. PICOGREEN analysis also reveals high concentrations of dsDNA in the non-aqueous fraction and a 10-fold reduction in raw lysate to aqueous phase dsDNA concentration.

Example 10: Impurity Removal Using a Hydrophobic Interaction Membrane

Figure 1B:
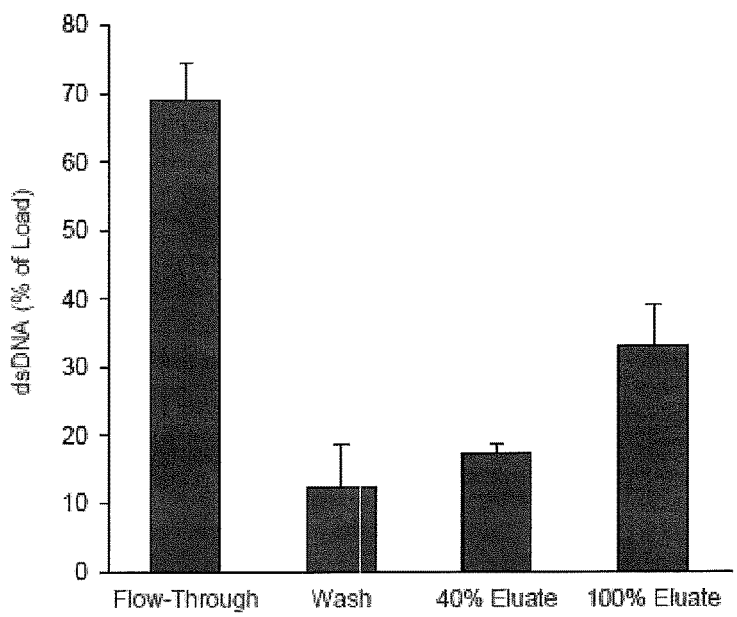

AAV3-like capsid-containing material in 1.25 M ammonium sulfate was loaded onto a phenyl membrane and eluted using a step gradient to 40% and 100% 20 mM Tris pH 7.0. The load, flow-through, wash, 40% eluate, and 100% eluate fractions were then assayed for dsDNA via PICOGREEN, and host-cell protein via ELISA. This analysis indicated a greater than 90% reduction in total host cell protein from the load to the 40% elution fraction (FIG. 1A), and a greater than 80% reduction in dsDNA from the load to the 40% elution fraction (FIG. 1B, n=2). The 40% elution fraction contained an average of 90% of loaded particles, while the 100% elution fraction contained less than 10% of loaded particles.

Example 11: Binding and Elution of Different Serotypes of AAV Using a Hydrophobic Interaction Membrane AAV1 or AAV5 containing cell culture medium or cell lysate was applied to a phenyl membrane and eluted using 20 mM Tris-HCl pH 7.0. The concentration of AAV capsids in the load, flow-through and elution fractions was measured using AAV1 or AAV5 capsid ELISA. AAV1 was efficiently captured and eluted, with an average recovery of over 90% from lysate and over 85% for media loads. AAV5 was bound and recovered slightly less effectively, with over 85% recovered in lysate and 70-80% recovered in media (Table 1).

TABLE 1

| Serotype | Media (% Recovery) | Lysate (% Recovery) |
| --- | --- | --- |
| AAV1 | 87.5 ± 1.5 | 94.7 ± 5.1 |
| AAV3-like | 89.5 ± 7.5 | 97.3 ± 12.5 |
| AAV5 | 76.8 ± 6.5 | 88* |
| AAV8 | 101.4 ± 11.6 | 91.6 ± 0.5 | n = 2 except where denoted by (*)

Example 12: Method for Harvest, Lysis, and Integrated Purification of AAV

Small-scale Harvest. To recover AAV from the 293 producer cells only, culture medium was decanted and discarded. Cells were lysed on a 10 cm plate or after detachment. To lyse on the plate, the appropriate salt was added directly to the plate, followed by aspiration of the lysate. For lysis after detachment, cells were removed from the plate with the addition of phosphate-buffered saline (PBS) and 5 mM EDTA (PBS-EDTA). The detached cells were subsequently decanted and mixed with salt at the concentration required for lysis. For cells lysed with ammonium sulfate, a final concentration of between 1 and 1.5 M at a pH between 6.5 and 7.5 was assessed. For cells lysed with sodium chloride, a concentration of 3 or 5 M at pH 7 was used.

To recover AAV from cell culture medium only, the medium was decanted and concentrated salt was added directly to the desired concentration, while culture plates with attached cells were discarded.

To recover AAV from both the producer cells and the cell culture medium simultaneously, cells were detached with PBS-EDTA and combined with decanted medium. Concentrated salt was then added to the desired concentration to lyse the cells.

Large-Scale Harvest.

To harvest AAV from a 10 layer cell stack, culture medium was decanted and 500 mL of PBS-EDTA was added to the cell stack to detach cells using vigorous agitation. Cells in PBS-EDTA were decanted and 3.5 M ammonium sulfate with 60 mM Tris at pH 7 was added to a final concentration of 1.25 M ammonium sulfate. The solution was mixed by inverting to lyse the cells and the resulting lysate was incubated without agitation for a minimum of 12 hours at 4° C. to allow for separation of insoluble material. Insoluble material was then removed using physical separation (e.g., pipetting). To harvest AAV from cells and culture medium simultaneously, cells harvested in PBS-EDTA were combined with culture medium and the salt concentration was adjusted to 1.25 M ammonium sulfate at pH 7.

Clarification and Chromatography.

To achieve a seamless and integrated process from lysis to membrane capture, either lysate, medium, or lysate combined with medium was clarified through an appropriately sized filter with a minimum pore size of 0.22 microns. This clarified material was then applied directly to a SARTOBIND Phenyl hydrophobic interaction membrane. A flow rate of between 1.7 to 5 membrane volumes (MV) per minute was used for all steps. The membrane was equilibrated in 15 MV of buffer thereby matching the salt concentration of the applied sample (e.g., 1.25 M ammonium sulfate with 20 mM Tris, pH 7). Following sample application, the membrane was washed in 20 MV of equilibration buffer and the bound species were eluted using a step or linear gradient to a buffer containing 20 mM Tris pH 7.

What is claimed is:

1. A method for isolating AAV particles grown in a cell culture comprising:
   (a) lysing, at or below room temperature and in the absence of a detergent, a suspension of producer cells comprising AAV particles with an effective amount of a lyotropic salt that promotes cell lysis and release of the AAV particles from the producer cells while maintaining producer cell DNA in a substantially intact state; and
   (b) separating insoluble producer cell DNA and cellular debris from the AAV particles thereby isolating the AAV particles,
   wherein said method is carried out in the absence of a nuclease, sonication, microfluidization, protease or organic solvent or one or more cycles of freezing and thawing.

2. The method of claim 1, wherein the lyotropic salt comprises:
   (a) a cationic component selected from the group consisting of $NH_4^+$, $K^+$, $Na^+$, $Li^+$, $Mg^{2+}$, $Ca^{2+}$ and guanidinium; and
   (b) an anionic component selected from the group consisting of $F^-$, $SO_4^{2-}$, $HPO_4^{2-}$, acetate, $Cl^-$, $NO_3^-$, $ClO_3^-$, $I^-$, $ClO_4^-$, and $SCN^-$.

3. The method of claim 2, wherein the lyotropic salt is ammonium sulfate.

4. The method of claim 3, wherein the concentration of ammonium sulfate is between 250 mM and 2000 mM.

5. The method of claim 2, wherein the lyotropic salt is sodium chloride.

6. The method of claim 5, wherein the concentration of sodium chloride is between 3000 mM and 5000 mM.

7. The method of claim 2, wherein the pH of the lyotropic salt is about 7.0.

8. The method of claim 1, wherein the insoluble producer cell DNA and cellular debris are separated from the AAV particles using a physical separation technique.

9. The method of claim 8, wherein the physical separation technique is selected from the group consisting of centrifugation, filtration, skimming, separation funnel separation, mixer-settler separation, and liquid-liquid extraction.

10. The method of claim 1, further comprising
    (c) subjecting the isolated AAV particles of step (b) to chromatography on a hydrophobic interaction chromatography adsorbent; and
    (d) recovering an eluate from the hydrophobic interaction chromatography adsorbent that contains substantially purified AAV particles.

11. The method of claim 10, wherein the hydrophobic interaction chromatography adsorbent comprises a butyl ligand, octyl ligand, phenyl ligand, bi-phenyl ligand, or combination thereof.

12. The method of claim 10, wherein the hydrophobic interaction chromatography adsorbent comprises a membrane or bead matrix.

13. The method of claim 1, wherein the suspension of producer cells and AAV particles comprises cell culture medium.

14. The method of claim 1, wherein the suspension of producer cells and AAV particles comprises a buffer.

15. A method for purifying AAV particles grown in a cell culture consisting essentially of:
    (a) lysing, at or below room temperature and in the absence of a detergent, a suspension of producer cells comprising AAV particles with an effective amount of a lyotropic salt that promotes cell lysis and release of the AAV particles from the producer cells while maintaining producer cell DNA in a substantially intact state;
    (b) separating insoluble producer cell DNA and cellular debris from the AAV particles to obtain isolated AAV particles;
    (c) subjecting the isolated AAV particles of step (b) to chromatography on a hydrophobic interaction chromatography adsorbent; and
    (d) recovering an eluate from the hydrophobic interaction chromatography adsorbent that contains substantially purified AAV particles,
    wherein said method is carried out in the absence of a nuclease, sonication, microfluidization, protease or organic solvent or one or more cycles of freezing and thawing.

* * * * *